United States Patent [19]

Kulprathipanja

[11] Patent Number: 4,857,642
[45] Date of Patent: Aug. 15, 1989

[54] PROCESS FOR SEPARATING ARABINOSE FROM A MIXTURE OF OTHER ALDOSES

[75] Inventor: Santi Kulprathipanja, Hoffman Estates, Ill.

[73] Assignee: UOP, Des Plaines, Ill.

[21] Appl. No.: 948,382

[22] Filed: Dec. 31, 1986

[51] Int. Cl.$^4$ .................... C07H 1/06; C13D 3/12; C13K 13/00

[52] U.S. Cl. .................... 536/127; 536/124; 536/1.1; 127/46.1; 127/46.3

[58] Field of Search .................... 536/124, 127, 1.1; 127/46.1, 46.3

[56] References Cited

U.S. PATENT DOCUMENTS

| | | | |
|---|---|---|---|
| 2,524,414 | 10/1950 | Wolfrom | 536/127 |
| 2,882,244 | 4/1959 | Milton | 252/455 |
| 2,883,244 | 4/1959 | Berger | 308/6 |
| 3,120,007 | 2/1964 | Perinich | 5/119 |
| 3,130,007 | 4/1964 | Breck | 23/113 |
| 3,160,624 | 12/1964 | Iwai et al. | 260/209 |
| 4,024,331 | 5/1977 | Neuzil et al. | 536/1 |
| 4,226,977 | 10/1980 | Neuzil et al. | 536/127 |
| 4,238,243 | 12/1980 | Tu et al. | 536/127 |
| 4,287,001 | 9/1981 | Kulprathipanja et al. | 536/127 |
| 4,295,994 | 10/1981 | Kulprathipanja | 536/127 |
| 4,298,501 | 11/1981 | Kulprathipanja | 536/127 |
| 4,325,742 | 4/1982 | Arena | 536/1.1 |
| 4,337,171 | 6/1982 | Kulprathipanja et al. | 536/1.1 |
| 4,340,724 | 7/1982 | Neuzil et al. | 536/127 |
| 4,442,285 | 4/1984 | Neuzil et al. | 536/127 |
| 4,444,961 | 4/1984 | Timm | 526/88 |
| 4,471,114 | 9/1984 | Sherman et al. | 536/127 |
| 4,516,566 | 5/1985 | Chao et al. | 536/127 |

OTHER PUBLICATIONS

P. Jandera et al., I. of Chromatography, 98, (1974, 55–104, p. 81.

*Primary Examiner*—Ronald W. Griffin
*Assistant Examiner*—Nancy S. Carson
*Attorney, Agent, or Firm*—Thomas K. McBride; John F. Spears, Jr.; Jack H. Hall

[57] ABSTRACT

A process for the liquid phase adsorptive separation of arabinose from an aqueous feed mixture of monosaccharides containing arabinose along with other aldoses and ketoses. The feed is contacted with an ammonium X-type zeolite. Arabinose is selectively absorbed to the substantial exclusion of other aldoses and ketoses and thereafter is recovered in high purity by desorption with water. The process can be carried out on a commercial scale by means of a simulated moving bed flow scheme.

8 Claims, 3 Drawing Sheets

1

PROCESS FOR SEPARATING ARABINOSE FROM A MIXTURE OF OTHER ALDOSES

BACKGROUND OF THE INVENTION

1. Field of the Invention

The field of art to which this invention pertains is the solid bed adsorptive separation of monosaccharides. More specifically, the invention relates to a process for separating arabinose from a mixture comprising arabinose and one or more additional aldoses, which process employs an adsorbent comprising a crystalline aluminosilicate, X-type faujasite to selectively adsorb arabinose from the feed mixture.

2. Description of the Prior Art

It is known that zeolites can be used to separate specific monosaccharides or classes of monosaccharides from carbohydrate feed mixtures. A specific example of a class separation is given in U.S. Pat. No. 4,024,331 disclosing the separation of ketoses from a mixture of ketoses and aldoses using a type X zeolite. Specific ketoses such as fructose can be separated from a feed mixture containing the same by an adsorptive separation process using an X or Y zeolite exchanged with selected cations at the exchangeable cation sites as disclosed in U.S. Pat. No. 4,340,724 to Neuzil et al. In the case of the X zeolite, barium, sodium and strontium ions are set forth. The Y-zeolite may be exchanged with ammonium, sodium, potassium, calcium, strontium, barium and combinations.

This invention is particularly concerned with the separation of arabinose from other monosaccharides. Obtaining pure arabinose has commercial significance in light of its potential as a starting material for the production of L-glucose, a possible nonnutritive sweetener. A common source of arabinose is the hydrolysis of hemicellulose in making pulp from wood or as a product of the conversion of plant tissue to sugars in biomass operations. Regardless of the source, L-arabinose is typically found in a mixture of many monosaccharides. Therefore, it is highly desirable to have a simple method for separating arabinose from the other monosaccharides present in the source mixture. However, in light of the ultimate food use of arabinose, the separation process must not provide contaminants that will render the arabinose or subsequent products unsuitable for human consumption.

Specific methods for separating arabinose are known in the art. U.S. Pat. No. 3,160,624 discloses the separation of D(L)-arabinose from D(L)-ribose by chromatography using a cellulose powder or ion exchanged resin. However, it is well known in the art that heretofore resin or cellulose adsorbents posed significant operational problems when their use is attempted on a large scale due to the high pressure drops associated with their use. However, newly developed methods of forming the ion exchange resins into very uniform spheres, as in U.S. Pat. No. 4,444,961 referred to hereinafter, reduce this tendency to cause high pressure drops. The zeolite adsorbents which are commonly used in large scale adsorptive separation processes have also been applied to the separation of arabinose from other mixtures of monosaccharides.

U.S. Pat. No. 4,516,566, is directed to the separation of L-arabinose from a mixture of sugar that exists in the hydrolysates of wood and beet pulp using water as the desorbent, with an X-type zeolite exchanged with barium cations.

Additional data related to potential adsorbents for a two-stage separation of arabinose from other monosaccharides is set forth in U.S. Pat. No. 4,471,114 insofar as it is pertinent, at column 7, lines 31-34. The passage just referred to relates to the use of a barium-exchanged Y-type faujasite. Due to the toxic properties of barium, this separation process will be difficult to apply when attempting to obtain food grade arabinose. It is also stated that $NH_4$-X zeolite is not suited to the separation of mannose from other monoscaccharides (column 7, lines 40-44).

A calcium-exchanged ion exchange resin (Dowex 50-W-X8) has been reported to separate arabinose from xylose sugars. P. Jandera et al., I. of Chromatography, 98 (1974) 55-104, p. 81.

In contradistinction to these findings, it has been discovered that X-type faujasites containing ammonium ions at cation exchanged sites are suitable adsorbents for the separation of arabinose from other monosaccharide aldoses. Moreover, the use of these zeolites with ammonium cations allows the purification of arabinose in a process that is acceptable for the food industry.

SUMMARY OF THE INVENTION

It is accordingly a broad objective of the present invention to provide a process for the separation of arabinose from a feed mixture containing arabinose and other ketoses and/or aldoses using an X-type zeolite with ammonium cations at cation exchanged sites.

In brief summary, the present invention is a process for separating arabinose from a feed mixture comprising arabinose and at least one other monosaccharide selected from the group consisting of aldopentoses, ketohexoses and/or aldohexoses. The process comprises contacting at adsorption conditions the monosaccharide mixture with an adsorbent comprising a type X zeolite containing ammonium cations at the exchangeable cationic sites, selectively adsorbing arabinose to the substantial exclusion of the other monosaccharides, removing the nonadsorbed portion of the feed mixture from contact with the adsorbent, and thereafter recovering a purified arabinose by desorption at desorption conditions. Because of the aformentioned potential value of the L-sugars, it is intended that, any specific reference to any monosaccharide herein, shall encompass both the L- and the D-forms. Other objectives and embodiments of the present invention relate to specific feed mixtures, adsorbents, desorbent materials, operating conditions and flow configurations all of which are hereinafter disclosed in the following discussion of the present invention.

DESCRIPTION OF THE INVENTION

Figure 1:
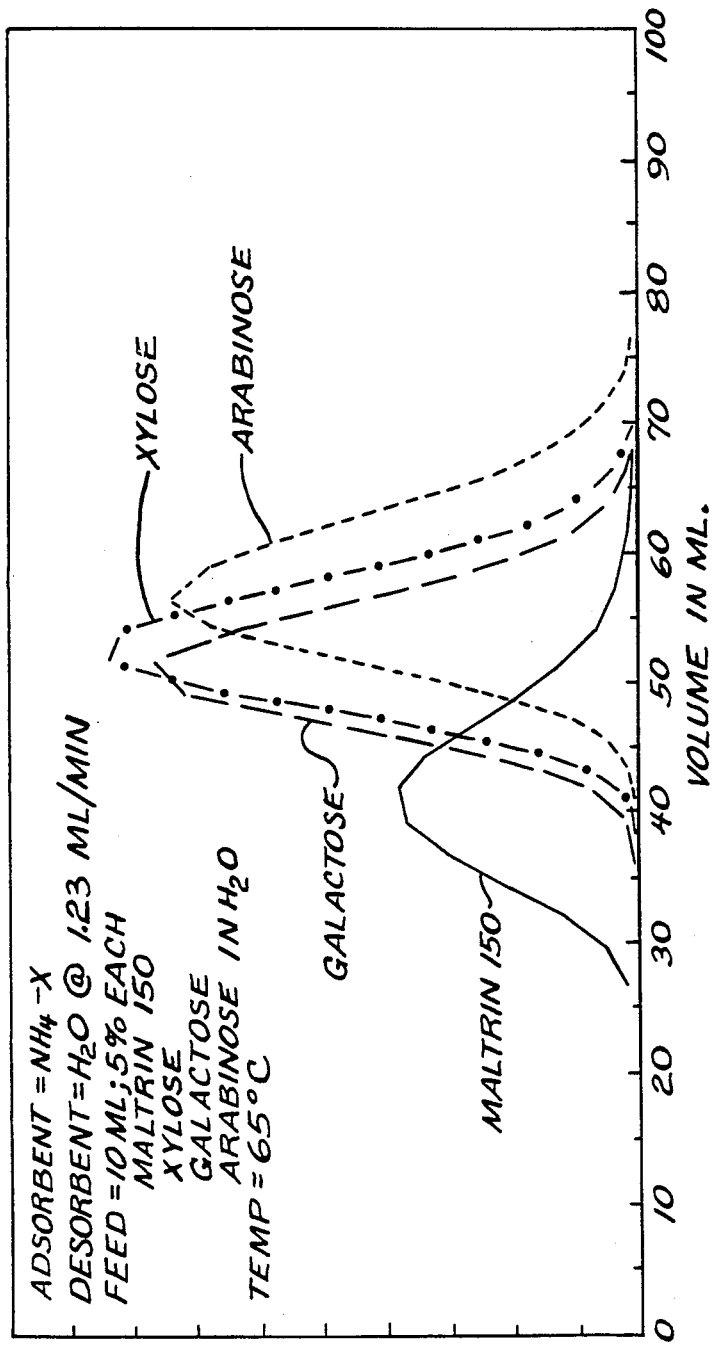
FIG. 1 is a plot of the pulse test of Example I to show the separation of arabinose from other sugars using an $NH_4$-exchanged X zeolite adsorbent.

At the outset the definitions of various terms used throughout the specification will be useful in making clear the operation, objects and advantages of my process.

A "feed mixture" is a mixture containing one or more extract components and one or more raffinate components to be separated by this process. The term "feed stream" indicates a stream of a feed mixture which passes to the adsorbent used in the process.

An "extract compohent" is a component or type of component that is more selectively adsorbed by the adsorbent while a "raffinate component" is a component that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators or evaporators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream.

The adsorbent materials of this invention comprise type X crystalline aluminosilicates having ammonium cations at cation exchange sites. The type X crystalline aluminosilicates or zeolites can be further classified as faujasites. As in the general case of all zeolites, these crystalline compounds are described as a three-dimensional network of fundamental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension. Zeolites are more fully described and defined in U.S. Pat. Nos. 2,882,244 and 3,130,007, respectively, incorporated herein by reference thereto. The X zeolites in the hydrated or partially hydrated form can be represented in terms of mole oxides as shown in Formula 1 below:

Formula 1

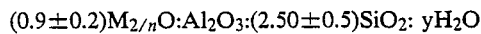
$(0.9\pm0.2)M_{2/n}O:Al_2O_3:(2.50\pm0.5)SiO_2: yH_2O$

The electrovalence of the tetrahedra is balanced by the cation "M" of the above equation which occupies exchangeable cationic sites in the zeolite. These cations, which after initial preparation are predominantly sodium, may be replaced with other cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed and dried to a desired water content. By such methods, the sodium cations and any nonsodium cations which might be occupying exchangeable sites as impurities in a sodium X zeolite can be partially or essentially completely replaced with other cations It is essential that the zeolite used in the process of my invention contains ammonium cations at exchangeable cationic sites.

Typically, adsorbents used in separative processes contain zeolite crystals and amorphous material. The zeolite will typically be present in the adsorbent in amounts ranging from about 75 wt. % to about 98 wt. % based on volatile free composition. The remainder of the adsorbent will generally be amorphous material such as silica, or silica-alumina mixtures or compounds, such as clays, which material is present in intimate mixture with the small particles of the zeolite material This amorphous material may be an adjunct of the manufacturing process for zeolite (for example, intentionally incomplete purification of either zeolite during its manufacture), or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The adsorbent used in my process will preferably have a particle size range of about 16–40 mesh (Standard U.S. Mesh). We have found that X zeolites with ammonium cations and amorphous binders possess the selectivity and other necessary requirements previously discussed and are therefore suitable for use in my process.

Certain carbohydrates or so-called simple sugars are classified as monosaccharides. These monosaccharides are hydroxyaldehydes or hydroxyketones containing one ketone or aldehyde unit per molecule and two or more alcohol functions. Thus, monosaccharides are classified as aldoses or ketoses on the basis of their carbonyl unit. Ketoses and aldoses are further classified by their carbon skeleton length. Accordingly, 5 carbon and 6 carbon monosaccharides receive the respective names of pentoses and hexoses. Well known aldohexoses include glucose, mannose and galactose. Arabinose and xylose are well known aldopentoses. Fructose is a well known ketohexose. This invention is a process for separating arabinose from other aldopentoses, ketohexoses and aldohexoses.

Consequently, feed mixtures which can be utilized in the process of this invention will comprise a mixture of arabinose and at least one other aldose. Potential feed mixtures containing substantial quantities of aldoses to the substantial exclusion of other monosaccharides are typically found in plant tissue hydrolysates. Such mixtures will usually contain significant quantities of such monosaccharides as xylose, arabinose, mannose, glucose, rhamnose and galactose. Apart from these more common sugars, feed mixtures derived from natural sources will also contain quantities of lesser known monosaccharides. A typical feed mixture for this invention will contain 20–30% xylose, 15–20% arabinose, 0.5–3% mannose, 40–60% glucose, and 1–5% galactose in respective proportions, based on weight percent of solids. In addition, there may be up to 10 wt. % solids of other lesser known sugars. However, this invention is not limited to the separation of naturally derived feed mixtures, but also includes separating arabinose from other aldoses in sugar mixtures that are synthetically prepared or produced by the processing of carbohydrates.

Although it is not clear what properties of the adsorbent are responsible for the arabinose separation herein described, it appears that it cannot be attributed to pore size selectivity. Since arabinose is separated from sugar molecules of similar size, it appears that electrostatic attraction plays an important role in the separation. While it is not possible to conclusively set forth the molecular interaction responsible for the adsorption, one possible explanation is an electrostatic interaction of cation in the adsorbent with the different orientation of specific sugar molecules. This varied orientation can provide a suitable disposition of the particular structural configuration corresponding to certain sugar molecules which is altered by the presence of specific cations in the adsorbent. Therefore, electrostatic interaction may provide the mechanism for this separation.

Although it is possible by the process of this invention to produce high purity arabinose, it will be appreciated that an extract component is never completely adsorbed by the adsorbent, nor is a raffinate component completely nonadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed arabinose to the concentration of less selectively adsorbed sugars will be highest in the extract stream, next highest in the feed mixture, and lowest in the raffinate stream. Likewise, the ratio of the less selectively adsorbed sugars to the more selectively adsorbed arabinose will be highest in the raffinate stream, next highest in the feed mixture, and the lowest in the extract stream.

Desorbent materials used in various prior art adsorptive separation processes vary, depending upon such factors as the type of operation employed. In the swing bed system, in which the selectively adsorbed feed component is removed from the adsorbent by a purge stream, desorbent selection is not as critical. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail, it is preferred that the adsorbent be more selective for all of the extract components with respect to a raffinate component than it is for the desorbent material with respect to a raffinate component. Secondly, the desorbent material must be compatible with the particular adsorbent and the particular feed mixture. More specifically, it must not reduce or destroy the critical selectivity of the adsorbent for an extract component with respect to a raffinate component. Additionally, the desorbent material should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent material, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods, such as reverse osmosis, may also be employed alone or in combination with distillation or evaporation. Since the raffinate and extract products are foodstuffs intended for human consumption, the desorbent material should also be nontoxic. Finally, desorbent materials should also be materials which are readily available and therefore reasonable in cost. A suitable desorbent for this separation comprises water, although ethanol or mixtures with water are useable.

The prior art has recognized that certain characteristics of adsorbents and desorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

$$\text{Selectivity} = (B) = \frac{[\text{wt. percent } C/\text{wt. percent } D]_A}{[\text{wt. percent } C/\text{wt. percent } D]_U}$$

where C and D are two components of the feed represented in weight percent and the subscripts A and U represent the adsorbed and unadsorbed phases, respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or nonadsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity the easier the separation is to perform. Higher selectivities permit a smaller amount of adsorbent to be used. The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Resolution is a measure of the degree of separation of a two-component system, and can assist in quantifying the effectiveness of a particular separation. Resolution for purposes of this application is defined as the distance between the two peak centers divided by the average widths of the peaks at ½ the peak height as determined by the pulse tests described hereinafter. The equation for calculating resolution is thus:

$$R = \frac{L_2 - L_1}{\frac{1}{2}(W_1 + W_2)}$$

where $L_1$ and $L_2$ are the distance, in ml, respectively, from a reference point, e.g., zero to the centers of the peaks and $W_1$ and $W_2$ are the widths of the peaks at ½ the height of the peaks.

The adsorption-desorption operations may be carried out in a dense fixed bed which is alternatively contacted with a feed mixture and a desorbent material in which case the process will be only semicontinuous. In another embodiment, generally referred to as a swing bed system, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid stream. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—a New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

While this invention may be practiced in any type of flow system, the manner of operation will affect desorbent selection. Swing bed systems are less sensitive to desorbent selection so that the process is likely to perform well with any material from the aforementioned broad class of desorbents. However, in adsorptive separation processes which are generally operated continuously at substantially constant pressures and temperatures to ensure liquid phase, the desorbent material relied upon must be selected more judiciously. It is in the continuous separation processes where the previously described class of preferred desorbents will offer the greatest advantages.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is required for this process because of the lower temperature requirements and because of the higher yields of extract product that can be obtained with liquid-phase operation over those obtained with vapor phase operation. Adsorption conditions will include a temperature range of from about 20° C. to about 200° C. with about 20° C. to about 100° C. being preferred and a pressure range of from about atmospheric to about 500 psig with from about atmospheric to whatever pressure is required to ensure liquid phase being preferred. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

A dynamic testing apparatus may be employed to test various adsorbents with a particular feed mixture and desorbent material to measure the adsorbent characteristic of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a nonadsorbed polysaccharide tracer maltrin, arabinose, one or more additional aldoses and other trace sugars, all diluted in desorbent, is injected for a duration of several minutes. Maltrin is a commercially available mixture containing 88% saccharides having a degree of polymerization of 4 or more (DP4+), 8.1% maltotriose, about 3% maltose and less than 2% glucose. Desorbent flow is resumed, and the tracer and the aldoses are eluted as in a liquid-solid chromatographic operation. The effluent is collected in fractions and analyzed using chromatographic equipment and traces of the envelopes of corresponding component peaks are developed.

From information derived from the test, adsorbent performance can be rated in terms of retention volume for an extract or a raffinate component, selectivity for one component with respect to the other, resolution of one component with respect to another, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. Resolution measures the degree of separation of two components. It is expressed as a ratio of the distance between the centers of the two peak envelopes to the average widths of the peaks at half the peak height. The rate of exchange of an extract component with the desorbent can generally be characterized by the width of the peak envelopes at half intensity. The narrower the peak width the faster the desorption rate.

The examples shown below are intended to further illustrate the process of this invention and are not to be construed as unduly limiting the scope and spirit of said process. The example presents test results for the invention when using the above dynamic testing apparatus.

EXAMPLE I

In this example, a pulse test was run using an X-type zeolite having ammonium ions at cation exchange sites to determine the separation of arabinose from a carbohydrate mixture. The $NH_4^+$-exchanged X-type zeolite of this example was bound in a clay binder and had an average bulk density of 0.8 gm/ml. The adsorbent was packed in an 8.4 mm diameter column having a total volume of 70 cc. The feed mixture consisted of 10 ml of the carbohydrate mixture given in Table 1 diluted with 80 ml of distilled water resulting in a solution containing 20% of solids.

TABLE 1

| | Wt. % Dry Solids |
|---|---|
| Xylose | 5 |
| Arabinose | 5 |
| Galactose | 5 |
| Maltrin 150 | 5 |
| Water | 80 |
| | 100 |

The experiment began by passing a water desorbent through the column at a flow rate of 1.23 cc/min. and a temperature of 65° C. At a convenient time 10 ml of feed were injected into the column after which the flow of desorbent was immediately resumed. FIG. 1 provides a graphical representation of the adsorbent's retention of arabinose compound to the other carbohydrates in the feed mixture.

A consideration of the average midpoint for each concentration curve reveals a good separation of arabinose from the other feed mixture sugars. Arabinose is clearly the most selectively retained component. While a substantial portion of the arabinose curve does lie within the xylose-galactose curve, this is due to the large volume of the unseparated xylose and galactose present in the feed and does not indicate an inability to perform the separation. From the net retention volumes and peak widths at half-height obtained from this experiment the selectivities and resolution of Table 1 were calculated.

TABLE 2

| Component Name | Net Retention Volume | Peak Width at Half-Height | Separation Factor (Beta) | Resolution Factor (.5 Height) |
|---|---|---|---|---|
| Maltrin 150 | 0 | 14.9 | Tracer | 1.13 |
| Xylose | 11.6 | 11.6 | 1.36 | .34 |
| Galactose | 9.9 | 11.4 | 1.60 | .48 |
| Arabinose | 15.8 | 13.1 | Refer. | Refer. |

These selectivities clearly establish the achievement of a high degree of separation for arabinose.

EXAMPLE II

Figure 2:
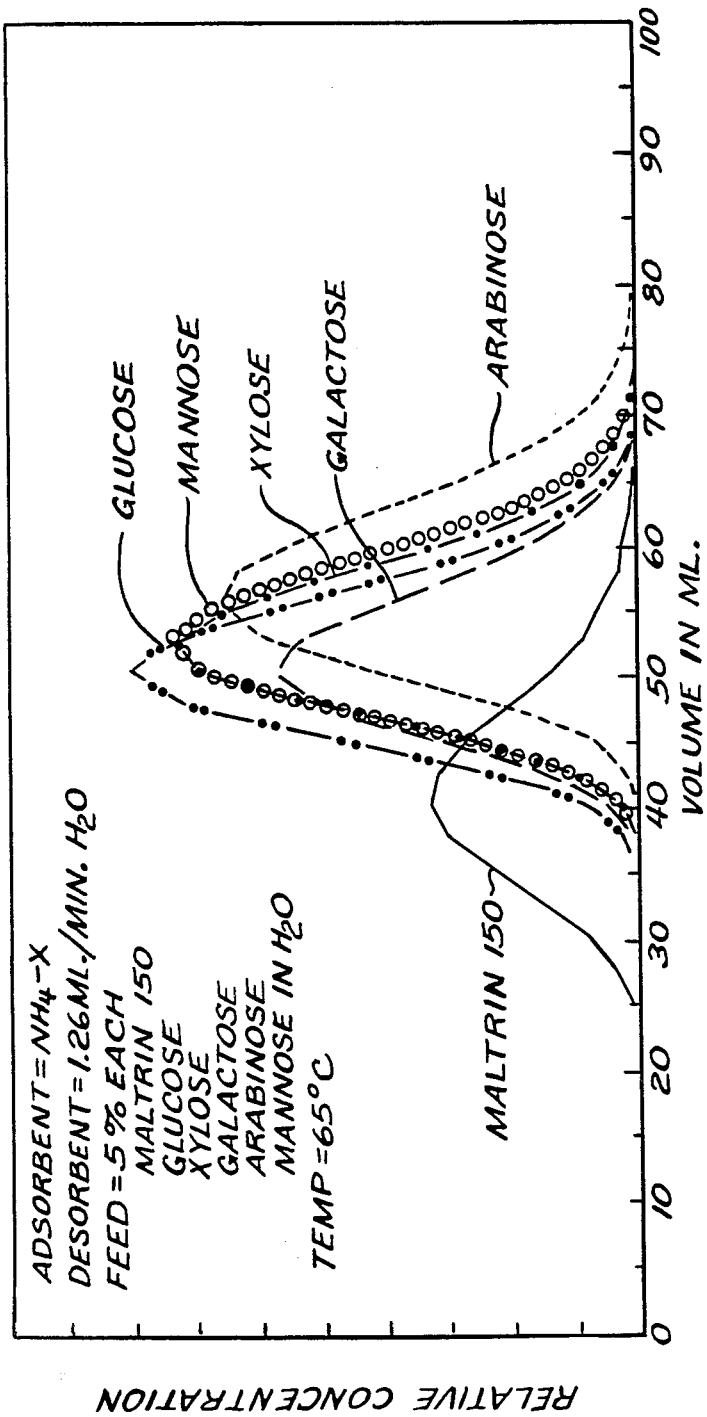
FIG. 2 is a plot of the pulse test in Example II to show the separation of arabinose from other aldoses and a ketose.

The separation is illustrated using other feed, comprising arabinose, mannose, xylose, glucose, galactose and Maltrin 150. Using the same procedure and testing apparatus as in Example I, the same adsorbent, $NH_4^+$-X, was used to separate the mixture in Table 3. The results are shown in FIG. 2.

TABLE 3

| Component Name | Net Retention Volume | Peak Width at Half-Height | Separation Factor (Beta) | Resolution Factor (.5 Height) |
|---|---|---|---|---|
| Maltrin 150 | 0 | 16 | Tracer | 1 |
| Glucose | 9.7 | 13 | 1.60 | .41 |
| Xylose | 11.6 | 13.2 | 1.34 | .28 |
| Galactose | 9.9 | 12.8 | 1.57 | .4 |
| Arabinose | 15.5 | 14.8 | Refer. | Refer. |
| Mannose | 12 | 13.8 | 1.29 | .24 |

EXAMPLE III

A pulse test, like Example II, was run on the same feed mixture as Example II, but with the X zeolite exchanged with tetramethyl quaternary ammonium ion, using a larger ion than $NH_4^+$. The results are shown in Table IV, following:

TABLE 4

| Component Name | Net Retention Volume | Peak Width at Half-Height | Separation Factor (Beta) | Resolution Factor (.5 Height) |
|---|---|---|---|---|
| Maltrin 150 | 0 | 16.8 | Tracer | .88 |
| Glucose | 11.2 | 14.7 | 1.28 | .2 |
| Xylose | 13.6 | 15 | 1.05 | .05 |
| Galactose | 9.1 | 13.3 | 1.57 | .36 |
| Arabinose | 14.3 | 15.6 | Refer. | Refer. |
| Mannose | 10.8 | 13.5 | 1.32 | .24 |

Figure 3:
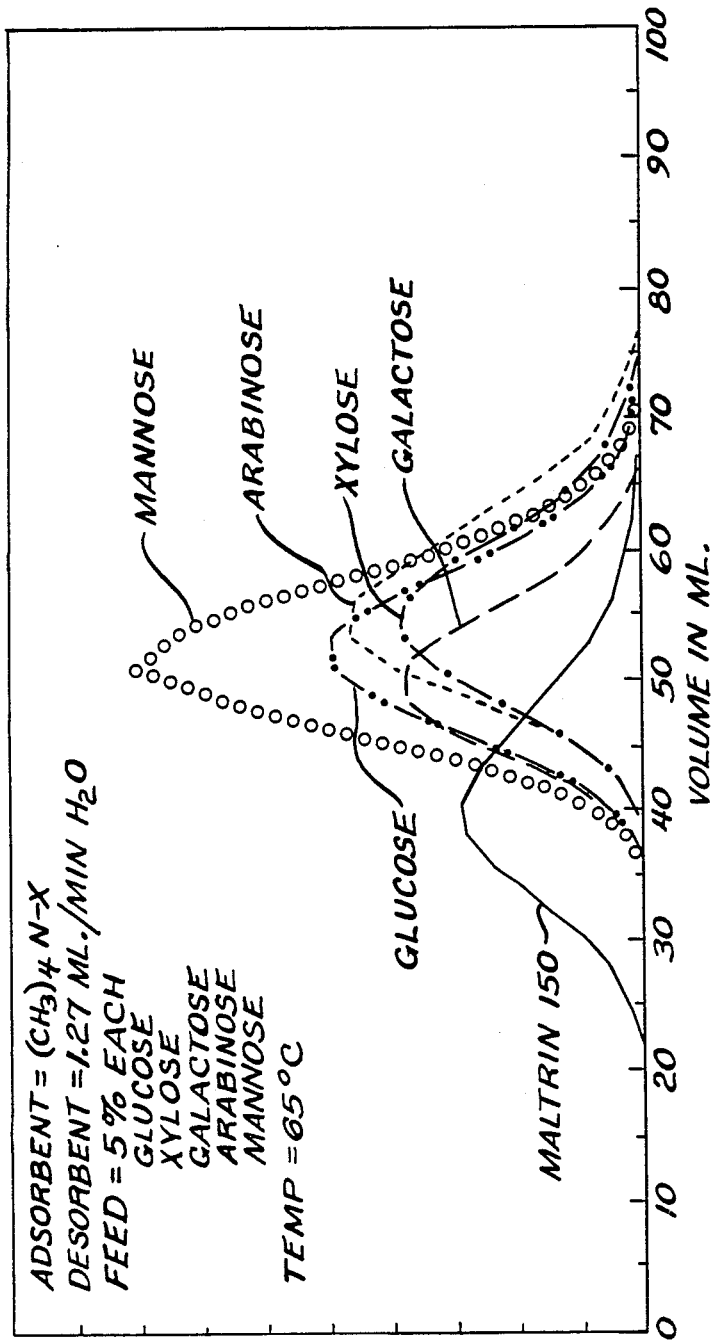
FIG. 3 is a plot of the pulse test in Example III using a molecule for the exchange ion that is very large compared to that of the invention.

Although net retention increased as predicted, resolution declined drastically, limiting the separation possible so that the results were considered unsatisfactory. The separation is plotted in FIG. 3.

What is claimed is:

1. A process for separating arabinose from an aqueous feed mixture containing arabinose and at least one other monosaccharide, selected from the group consisting of aldoses and ketoses, which comprises contacting at adsorption conditions said mixture with an adsorbent comprising a type X zeolite having ammonium cations at exchangeable cationic sites, selectively adsorbing said arabinose to the substantial exclusion of the other monosaccharides, removing the nonadsorbed portion of the feed mixture from contact with the adsorbent, and thereafter recovering high purity arabinose by desorption with a desorbent at desorption conditions.

2. The process of claim 1 wherein said feed mixture contains arabinose and at least one other monosaccharide selected from the group consisting of glucose, xylose, galactose, mannose and fructose.

3. The process of claim 1 wherein said desorbent comprises water.

4. The process of claim 1 wherein said separation is effected by means of a simulated moving bed flow scheme.

5. The process of claim 4 wherein said simulated moving bed scheme uses a countercurrent flow.

6. The process of claim 4 wherein said simulated moving bed scheme uses cocurrent flow.

7. The process of claim 1 wherein said adsorbent includes a binder comprising inorganic oxides selected from the group consisting of clay, alumina and silica.

8. The process of claim 1 wherein said adsorbent includes a binder comprising organic polymers selected from the group consisting of ethylcellulose, cellulose acetate and polystyrene.

* * * * *